United States Patent [19]

Rosenfield et al.

[11] 4,275,053

[45] Jun. 23, 1981

[54] BLOOD CELL TYPING AND COMPATIBILITY TEST PROCEDURE

[75] Inventors: Richard E. Rosenfield, Bronx; Shaul Kochwa, Queens, both of N.Y.

[73] Assignee: Mt. Sinai School of Medicine of the City University of New York, New York, N.Y.

[21] Appl. No.: 915,507

[22] Filed: Jun. 14, 1978

Related U.S. Application Data

[63] Continuation-in-part of Ser. No. 856,799, Dec. 2, 1977, abandoned, which is a continuation-in-part of Ser. No. 604,808, Aug. 14, 1975, abandoned.

[51] Int. Cl.³ .................... A61K 39/00; G01N 31/00
[52] U.S. Cl. ........................................ 424/12; 424/11
[58] Field of Search ................................ 424/12, 11

[56] References Cited

U.S. PATENT DOCUMENTS

| | | | |
|---|---|---|---|
| 3,639,558 | 2/1972 | Csizmas | 424/3 X |
| 4,002,532 | 1/1977 | Weltman | 424/12 |
| 4,011,308 | 3/1977 | Giaever | 424/12 |
| 4,041,146 | 8/1977 | Giaever | 424/12 |

OTHER PUBLICATIONS

Kennedy, *Immunology*, vol. 20, 1971, pp. 253-257.
Greeley, *The J. of Immunol.*, vol. 113, Dec. 1974, pp. 1883-1890.
Kodera, *Int. J. Cancer*, vol. 16, 1975, pp. 579-592.
Isliker, *Annals NY Acd Sc.*, Nov. 11, 1953, vol. 57, Art. 3, pp. 226-232.
Kovarik, *Arch. Path.*, vol. 86, 7/68, pp. 12-17, 19-21.
Molinaro, *Fed. Proc.*, vol. 32, Mar. 1973, Ab. No. 4169.
Molinaro, *Nature*, vol. 248, pp. 515, 1974.

*Primary Examiner*—Frederick E. Waddell
*Attorney, Agent, or Firm*—Brumbaugh, Graves, Donohue & Raymond

[57] ABSTRACT

A solid-phase blood typing procedure is described based upon either agglutination or immune lysis. In this invention, a monolayer of cells is irreversibly bound to a solid matrix, and thereafter a serum containing antibodies is brought into contact with the bound cell layer. Immuno-adsorption of antibodies by the bound cells occurs where the antigens of the cell membranes and the antibodies in the serum are complementary to each other. This antibody-sensitized monolayer of blood cells can either bind a second layer of blood cells carrying complementary antigen (solid-phase agglutination) or undergo lysis in the presence of serum lytic complement (solid-phase immune lysis). Carrying out these reactions with a monolayer of blood cells bound to a solid matrix allows quantitative evaluation of results by such standard instrumentable procedures as densitometric scanning, radioisotope counting, etc.

33 Claims, No Drawings

BLOOD CELL TYPING AND COMPATIBILITY TEST PROCEDURE

This is a continuation-in-part of our copending application, Ser. No. 856,799 filed Dec. 2, 1977, now abandoned which, in turn, was a continuation-in-part of our application Ser. No. 604,808, filed Aug. 14, 1975, now abandoned.

Many medical procedures require a determination of pre-transfusion or pre-grafting blood cell compatibility between donor and patient. Blood cell compatibility is determined by the non-occurrence of an immunological reaction between antibodies contained in the blood serum of a patient and antigens present on blood cells from a donor. For example, if the red cells of a patient are type A (i.e., have "A" antigens on the red cells), the serum of such a patient's blood will have anti-B antibodies, i.e., antibodies which will react with "B" cells. If such a patient receives a donation of "B" blood, an immunological reaction will occur between the anti-B antibodies of the patient's serum and the B-antigens of the red blood cells of the donor. Such an incompatibility can result in serious consequences because of intravascular hemolysis.

Test for blood cell typing and compatibility are generally of two types: (i) a test to determine whether a specific antibody added to the cells will cause their agglutination, and (ii) a test to determine whether a specific antibody added to the tested cells together with serum complement, will cause cell lysis.

The first of these two basic tests, agglutination, refers to a clumping of blood cells containing, for example, type A antigens, to which anti-A antibodies are added in the absence of complement. The A-antigen and the anti-A antibody react specifically with each other by immunological reaction with the antibody forming bridges between adjacent cells. This leads to an interlocked mass of the blood cells joined to each other by the added antibodies.

The second of the two tests referred to above, cell lysis, relates to the disruption of cell membranes leading to death of the cells and release of their intracellular contents. Cell lysis is the result of a reaction which occurs between cell membrane bound antibody and a group of potentially destructive proteins in normal serum (called "complement").

Both methods described above are used for the typing and compatibility testing of the cellular blood elements, erythrocytes, granulocytes, B and T lymphocytes, and platelets (thrombocytes). Although often used only qualitatively, both methods are intrinsically quantifiable and have been used separately for assay of antigen, antibody, and serum complement.

BACKGROUND OF THE INVENTION

In blood cell typing and compatibility test procedures commonly used in clinics today, both agglutination tests and cell lysis tests are carried out in a liquid phase, that is, sera containing antibodies with or without complement to be tested are mixed with suspensions of the blood cells with respect to which blood typing or compatibility testing is to be evaluated. Normally, fixed volumes are employed.

Evaluation of agglutination test results requires the technician to distinguish agglutination of cells due to specific antigen-antibody molecular bridging from non-specific cell aggregation in which unrelated forces also cause some degree of clumping. The technician must also be able to distinguish free unagglutinated cells which may be present from clumped or agglutinated cells. This requires highly experienced personnel or precise particle sizing and counting with costly instruments. In addition, measurement of the degree of specific agglutination is either poorly semi-quantitative or is costly and complicated to perform.

While some instrumented tests for typing of red blood cells by agglutination have been developed, the equipment for these procedures is both costly and complicated to use. For example, one device which has been proposed for typing red blood cells by instrument is known as the "AutoAnalyzer" of Berkman et al. described in Transfusion, Vol. 11, No. 6, pp. 317 et seq. (1971), and of Rosenfield et al. described in Vox. Sang. 26:289–333, 1974. In the AutoAnalyzer, blood samples and antibody sera are combined under special circumstances in complex tubular coils designed to bring about agglutination. The sample from the reaction coils passes a "T" connection with the leg in a downward position so that agglutinates which are formed tend to be removed. Agglutination can be detected measuring the decrease in optical density of the effluent from the "T" carrying the non-agglutinated fraction (Berkman et al. and Rosenfield et al.), or by trapping very strong agglutinates from the "T" on filter paper (Shield et al., Transfusion, Vol. 9, p. 348, 1969).

An alternative device is known as the "Groupamatic" and can cost several hundred thousand dollars (see Garretta et al., Vox Sang., Vol. 27, p. 141, 1974). In the Groupamatic device, sera and blood cell suspensions are combined to produce agglutination. The presence of agglutination is detected by passing the suspension across two light beams, one of which passes through the center of the reaction cuvette while the other passes through the periphery. A difference in the transmission of the beams is taken as the measure of the strength of agglutination. Sophisticated circuitry is required, however, placing the instrument beyond the means of all but the largest blood bank operations.

All liquid-phase hemagglutination tests, be they manual, "AutoAnalyzer", or "Groupamatic", suffer from a series of problems. Firstly, the manual tests lack the sensitivity of the instrumented tests so that clinically-significant red cell antigen-antibody reactions may be indiscernible by even the most experienced personnel. Secondly, unnecessary and unwanted protein in the reaction mixture may actually interfere with the development of hemagglutination, and cannot be removed readily without significant loss or elution of antibody. Thirdly, the red cells of about 2% of persons are unsuitable for sensitive evaluation by AutoAnalyzer (and presumably also by Groupamatic). Fourthly, red cells lose their sensitivity to specific hemagglutination on storage at 4° C., even for 2-3 weeks. Fifthly, not even the sensitive methods of Berkman et al. and Rosenfield et al. will detect all clinically-significant red cell antigen-antibody reactions. Lastly, "AutoAnalyzer" and "Groupamatic" tests are inefficient for the detection of minor cell population cohorts in samples containing mixtures of cells having different antigens. Even if a mixture is recognized, separation to allow separate measurement and assay of the cohorts is extremely tedious and can only be performed manually by the most experienced personnel.

Tests based upon immune lysis present no problems when the cell surface antigen-antibody reaction interacts efficiently with complement, as for tissue (e.g., HL-A) typing. Unfortunately, this is rarely true with human red cells where either the cell membrane antigen-antibody complex interacts inefficiently with complement or antibody concentration must be limited to prevent intense agglutination that will mechanically interfere with immune lysis.

These problems gravely affect the operation of blood banking serology laboratories where even routine red cell typing remains a time-consuming, manual operation that demands more skillful and experienced personnel than are available. Furthermore, relatively few blood banks can undertake lymphocytotoxic tests required for tissue typing. There are no direct immunologic tests available to determine the pre-transfusion compatibility of granulocytes, and only an indirect test for platelets, such as $^{14}$C-serotonin release. (While granulocytes and platelets may be assigned HL-A types by selected and appropriate tests, such typing will not guarantee their compatibility).

STATEMENT OF THE INVENTION

Broadly within the scope of the present invention, we have discovered that both agglutination and cell lysis test procedures on blood cells are significantly improved when a monolayer of reactive cells is irreversibly bound to a solid matrix. Thereafter that layer is contacted with a solution (or serum) containing antibodies potentially reactive by immunoadsorbence on the cell layer, and the extent to which immunoadsorbence occurs is determined.

Preferably, the extent of immunoadsorbence is determined by applying a second suspension of cells in an amount sufficient to form a second monolayer of cells on the primary cell monolayer containing immunoadsorbed antibody. The test is read by measuring the extent to which the second monolayer of cells is immunoadhered by antibody linking the two cell layers. Depending on test format, the procedure can be used to assay antigens in or carried by the cells forming either the first or second monolayers, antibodies immunoadsorbed by either the first or second cell monolayers, or compatibility between potential donors and recipients. The test format also can be adapted to assay extraneous soluble or insoluble antigens by competitive inhibition. Not only is the sensitivity of the test procedure increased, but the result of the immune reaction is readily measurable by simple instrumentation. Furthermore, the problems affecting liquid-phase tests are either minimized or abolished.

By irreversible bonding of cells to a solid matrix, we are referring to bonding of the reactive cells by molecular forces, such as the formation of covalent chemical bonds between sites on the cell surface and the reactive groups on the substrate, or to the formation of bonds by weaker molecular forces such as van der Waals forces, columbic forces or hydrogen bonding that will withstand the effects of further procedural conditions.

By way of a simple illustration, the blood typing test referred to above may be carried out in three steps: (1) a primary monolayer of erythrocytes (by way of illustration, reference will be made to type A) is bound irreversibly to a solid matrix; (2) using the cell monolayer as an immunoadsorbant, antibodies such as anti-A antibodies can be applied and adsorbed specifically; and (3) the antibody-coated primary monolayer may now be tested either for their susceptibility to immune lysis by complement (solid-phase lysis) or for their capacity to bind a second monolayer of target cells that carry appropriate antigens (solid-phase agglutination).

In the case of human erythrocytes, cell lysis by complement is not efficient. In this case, therefore, it is preferred to assay the presence of antibodies immunoadsorbed on the first cell monolayer by lysing the first cell monolayer with distilled water (to make it colorless), applying a second suspension of erythrocytes sufficient to form a second monolayer, and measuring the extent to which the second cell layer is cross-linked to the first cell layer by antibodies. There results a test slide of two cell monolayers, bound in an orderly one-cell-on-one-cell arrangement by an intervening layer of antibodies.

The test result may be evaluated in any convenient fashion, such as by examination under a microscope; however, of particular importance to the present invention is that the test results are especially suited to be evaluated by densitometric techniques using standard, and readily available, instruments. For solid-phase hemagglutination, the test plate prepared in the foregoing manner can be subjected to static or scanning densitometry at wave lengths where the hemoglobin content of the tested erythrocytes is absorbant to light (for instance, blue light having a wavelength of 415 nm is suitable). Scanning densitometry involves only the use of well-established laboratory equipment which is readily available and provides quantitative answers to questions such as (1) Is a second layer formed?; (2) How many cells does a second layer represent?; and (3) What is the distribution of the second layer? (By "distribution," reference is made to the uniformity of the second layer. A uniform second layer implies that 100% cells in the applied suspension carry the necessary antigen to bind to the first layer, whereas a non-uniform distribution implies the occurrence of some "negative" cells in the applied suspension).

The procedure of the present invention may be adapted to a variety of test formats depending upon whether antigens or antibodies are known. Under all formats, however, the qualitative and quantitative results of these tests are unaffected by unwanted proteins (they are washed away), or the age of the tested red cell sample in 4° C. storage. Moreover, we have found that even the red cells of persons unsuitable for evaluation by AutoAnalyzer can be assayed using the techniques of the present invention.

A. Direct Agglutination

1. Blood Typing. In blood typing, which is a primary application of the present invention, a monolayer of erythrocytes having a known type can be irreversibly bound on a suitable support. The complementary antibodies are immunoadsorbed, and the first monolayer of erythrocytes is hypotonically lysed to release the hemoglobin to render the layer transparent. (It is possible that lysis can be effected at an earlier stage of the process). Such a cell layer can be used to assay erythrocytes from a patient, a positive reaction being indicated by the formation of a second monolayer of erythrocytes.

2. Testing of Serum for Expected and Unexpected Agglutinins. A cell layer of a known type can be prepared to assay for antibodies in sera for the presence of antibodies. A positive reaction is indicated by the formation of a second monolayer of cells.

3. Compatibility Testing. Compatibility between patient and donor may be assayed. In this case, almost all of the antigenic determinants of the donor may be unknown. A first monolayer of erythrocytes (or other cells) from the donor is incubated against sera drawn from the patient. A second cell monolayer is then constructed (or attempted) by applying a second suspension of cells drawn from the donor. Incompatibility is indicated by the formation of a second cell layer.

B. Antiglobulin (Coombs) Tests

Antigens carried on cell surfaces which can be assayed by the present invention may be either an integral part of the cell membrane, an immunoadsorbed species carried on the cell surface, or a chemical structure bound to the cell surface.

1. Indirect Antiglobulin Tests a. Assay for Bound Immunoglobulins (Ig).
A first cell layer is formed either from cells exposed to a suspected source of antibodies or from normal cells. In the latter case, a serum suspected of containing antibodies is applied to the primary monolayer to allow immunoadsorption. The Fab portion of the immunoglobulin is immunoadsorbed by antigenic determinants on the cell surfaces. The Fc portion, however, is free and carries Ig antigenic determinants. After washing, the cell layer is now incubated with an anti-Ig reactive with the Fc portion of the antibody carried by the cells forming the first monolayer. In the case of the erythrocytes, the primary monolayer carrying both Ig and anti-Ig is now hypotonically lysed and a secondary source of cells, known to carry corresponding Ig on their surfaces, is applied and allowed to settle as a secondary cell layer. The extent of binding of the secondary cell layer is a measure of anti-Ig bound by the immunoadsorbed antibody of the primary cell monolayer.

b. Assay for fixation of specific complement components. The property of antibodies, immunoadsorbed by the primary cell monolayer, to bind complement components can be assayed by exposure of a primary monolayer carrying immunoadsorbed antibodies to a source of complement. After brief incubation and reduction of ionic concentration, specific antibodies to a selected complement component are applied. After washing and, in the case of erythrocytes, cell lysis, a second source of cells known to carry such complement component on their surfaces is applied. The degree of immunoadsorbence of anti-complement component antibodies determines the extent of binding of the second layer of complement component coated cells.

2. Direct Antiglobulin Tests. In acquired hemolytic anemia, the patient's red cells may carry immunoglobulins and/or complement components on their surfaces. These may be assayed directly and specifically by forming a primary cell monolayer of the patient's red cells and applying specific antisera (for example, anti-IgG, anti-IgA, anti-IgM, anti-C3, anti-C4, etc.). In the case of erythrocytes, the cell monolayer is hypotonically lysed. The capacity of the same cell (or others known to carry the tested structures) to adhere as a second cell layer, indicates that the primary cell monolayer carried the tested structure.

C. Analysis of Cell Samples Containing More than One Cell Population

1. Percent Cells in a Mixture. The present invention may be used to assay blood type in patients having two or more cell populations. This occurs, for example, in patients having a recent history of blood transfusion. Such a patient may have original type A erthrocytes and, in addition, type O erythrocytes from transfusions. A blood sample from such a patient, if applied to a primary type A cell monolayer carrying anti-A antibodies, will show an incompletely-formed second erythrocyte layer. The areas of bound, second layer erythrocytes represent the patient's original type A blood cells adherent to the first cell monolayer by means of anti-A antibodies. "Holes" represent areas where the transfused blood cells not carrying an A antigen had occupied a potential binding site, and were subsequently washed away prior to reading the test result. In such a case, the percentage of the test slide covered by the patient's type A blood cells measures the percent of the patient's blood which represents the original blood type.

2. Typing a Cell Cohort. The procedure of ¶ C.1 can be further extended to assay other antigenic determinants on one of the cohorts of such a blood sample. In further extending the procedure, the primary cell layer is repeatedly exposed to a suspension of the patient's blood cells until a second layer has been fully formed by adherent type A blood cells of the patient. The second layer is incubated against known antibodies to the antigenic determinant of interest. After the second layer has been lysed, the capacity to form a third layer of red blood cells known to carry this antigen indicates that the antigen was present on the cells of the second layer.

D. Inhibition by Soluble or Particulate Antigens

This assay comprises the steps of (a) applying to a solid matrix a first suspension of cells known to carry antigens to be tested under conditions effective to bind irreversibly a layer of said cells to said matrix; (b) contacting said layer (a) with a mixture of (i) a solution of an antibody reactive by immunoadsorption with antigen carried by the cells of said layer (a) and (ii) a second solution or suspension to be assayed for antigen by inhibition of the antibody in said solution (i); and (c) thereafter measuring the extent to which said antibody in solution (i) is bound by immunoadsorption to said layer (a).

The procedure of this invention can also be used to test solutions or suspensions of materials suspected of sharing antigenic properties. Inhibition or neutralization of the known antibodies by antigens present in the second solution or suspension will be reflected by a reduction or abolition in immunoadsorbence of known antibodies by the irreversibly bound cell monolayer.

DESCRIPTION OF THE PRIOR ART

Despite the long-standing clinical problems associated with blood banking serology, and the need to upgrade the procedures and make those procedures amenable to instrumentation and automatic techniques, there has been little assistance provided by the prior art to those in the field. For a number of years, there has been known the so-called "Eldon" cards for blood typing tests. These have been described, for example, in U.S. Pat. No. 2,770,572. The '572 patent describes a test card for use in typing human blood in which a support sheet bears on differing portions of its surface dried specimens of test sera containing antibody factors in a mixture with conglutinin or congulutinin substitutes. In effecting blood typing tests using the Eldon card, blood samples from the patient whose blood is to be typed are placed in droplets on the various serum spots contained on the card and examined, after allowing for appropriate reaction time, for the presence or absence of agglutination. The tests, however, are limited to anti-A, anti- B, and anti-Rh (Rh$_o$ or D), and even these are associated with significant errors in interpretation.

More recently, R. T. Price, in U.S. Pat. No. 3,666,421, has described another diagnostic test slide in which serological reagents are placed in drops upon a test slide and dried to a spot that may be subsequently reconstituted and reacted in an agglutination reaction for the identification of blood type (or other antigen-antibody reaction systems identifiable by agglutination). The test slide as described by Price, however, remains subject to the defects characteristic of ordinary liquid-phase agglutination: the test shows essentially only the presence or absence of agglutination and depends upon evaluation by skilled technicians to determine whether the agglutination is the result of specific antigen-antibody reaction or is simply the result of non-specific cell aggregation; it is difficult or impossible to evaluate whether free unagglutinated cells are present along with clumped cells of specific agglutinates.

James E. Smith, in U.S. Pat. No. 3,770,380, describes a device suggested for evaluating immune adherence reactions. It should be noted in this respect that the immune adherence reactions to which the Smith patent relates differ from the immunoadsorption phenomena on which the present invention is based. Immune adherence is the non-specific clumping of particles or cells due to the presence of complement; in immune adherence, it is the complement which causes binding. Immune adherence is characterized by non-specific reactions between the complement and the particles and cells to which they bind. Immunoadsorption, by contrast, is a specific binding between antigenic sites on a cell membrane and antibodies present in a serum. Thus, immunoadsorption, in contrast to immune adherence, refers to specific binding between antigens and antibodies.

The device described by Smith is a flat cell-like structure supplied on its floor with successive coatings of a bacteria or viral material as an overcoating, which is bound to the base of the cell by means of a transparent, dried protein underlayer. Immune adherence reactions between the bacteria or virus of the thus-prepared cell and red cells carrying antibody and complement in a test fluid applied thereto are then evaluated by determining the extent to which the specially-prepared red cells in the applied fluid adhere to the bacteria or virus containing overcoating. The procedure described by Smith has not found practical clinical value because immune adherence itself has not been widely adopted, and because immune adherence is non-specific, it is not suitable to evaluating specific antigen-antibody reactions.

A layer of blood cells imbedded in a solid support has been used for scientific purposes unrelated to blood typing and compatibility testing. Such layers are not bound by covalent or other molecular forces. Thus, Goodman (Nature, 193:350, 1962) prepared columns of formalinized human red cells imbedded in polyurethane which he used to fractionate human anti-red cell antibodies on the basis of the strength of their binding to the trapped red cells.

The principle of binding a prosthetic group (of an antigen, antibody, enzyme, etc.) to a solid matrix is a well-established biochemical method (see Cuatrecases and Anfinsen, Annu. Rev. Biochem., 40:259, 1971), and is widely used in solid-phase radioimmunoassay procedures (see, Brit. Med. Bull., 30:1-103, 1974). However, blood or other cells have not been bound irreversibly in a monolayer to a solid matrix to facilitate blood or tissue typing, compatibility testing, etc.

In a series of papers, Fagraeus and her co-workers studied mixed hemadsorption procedures in situations where the antigen was sessile on a glass surface. The work is generally summarized by Fagraeus, Espmark and Johnsson in "Mixed Hemadsorption. A Mixed Antiglobulin Reaction Applied to Antigens on a Glass Surface—Preparation and Evaluation of Indicator Red Cells; Survey of Present Applications", *Immunology*, V. 9, pp. 161–175 (1962). Monolayer cell cultures were prepared by conventional methods. After the cell sheet had become nearly confluent, antibody was applied by exposing the cultured cell layer to antiserum. The attachment of antibodies was then traced by mixed hemadsorption using red cells carrying an antiglobulin adsorbable by the antibody.

By way of specific illustration, Fagraeus et al. described the inoculation of a cultured cell layer with a vaccinia virus. Antibodies to the vaccinia virus were reacted with anti-vaccinia sera obtained from various animals, for example, rabbit. The cultures were then covered with a suspension of indicator cells.

Indicator cells were prepared by first coating sheep red blood cells with heat-inactivated amboceptor serum from the rabbit.* The coated cells were then contacted with an antiserum to rabbit immunoglobulin, which resulted in partial agglutination to prepare the indicator. The indicator particle was reactive with the anti-vaccinia antibodies to be visualized.

*If the anti-vaccinia serum is from another species, the first layer of amboceptor would be a gammaglobulin from the species whose anti-vaccinia serum is to be indicated. The second coating would then be an anti-immunoglobulin to that species.

In still another paper, "Mixed Agglutination with Platelets," Int. Arch. Allergy, V. 42, pp. 474-484 (1972), Juji, Kano and Milgrom employed mixed agglutination to detect cell surface antigens on platelets.

Juji el al. employed layers of platelets adhered to a glass surface. This adherence is a natural and unique property of platelets not shared by red cells. However, the naturally-occurring adherence was so fragile that the platelets had to be fixed by formalinization. Moreover, the quantity of platelets used in the Juji et al. work was such that the platelet layer was a number of cells thick.

The indicator erythrocytes employed by Juji et al. were similar to the indicator erythrocytes employed by Fagraeus et al. (supra). In brief, sheet rbcs were sensitized by rabbit anti-sheep erythrocyte serum and agglutinated by goat antiserum to the rabbit immunoglobulin. Human antibodies were detected by an indicator system prepared by sensitizing a suspension of Rh+ erythrocytes with anti-CD serum. The erythrocytes were washed and resuspended. The suspension was then agglutinated with rabbit antiserum to human immunoglobulin.

Juji et al. described a number of tests in which their procedure was employed to identify human leukocyte antigens on platelets by reaction of anti-HLA sera with the platelets. The occurrence or non-occurrence of an immunological reaction was traced both by mixed agglutination and by cytotoxicity with lymphocytes.

DETAILED DESCRIPTION OF THE INVENTION

Binding of a first monolayer. The following is a description of the invention with respect to presently-used tests of erythrocytes. Polystyrene test tubes are coated with fibrinogen (applying 0.5 mg/ml) which binds irreversibly. After washing away excess unwanted protein, polylysine (0.1 mg/ml) is applied to the bound fibrinogen. After further washing to remove excess polylysine, there is introduced a suspension of erythrocytes (RBC). These RBC are bound irreversibly (for purposes of testing) as a monolayer to the polylysine-fibrinogen-coated polystyrene surface.

A fibrinogen pre-treatment of a polystyrene substrate is effective to bind the polylysine rapidly and economically. Previous methods of binding polylysine to polystyrene by chemical treatment of the polystyrene surface have proved to be relatively time consuming and cumbersome.

The method of binding blood cells as a monolayer on a solid matrix need not be restricted to the above. The literature relating to coupling proteins to polymers (see Cuatrecases and Anfinsen, Annu. Rev. Biochem., 40:259, 1971) indicates that as an alternative, one may use preparations of polymers (sheets of polyurethane, polystyrene, etc.) that contain on their surface reactive groups such as glutaraldehyde, cyanogen bromide, amino or carboxyl groups, and others that will allow direct covalent coupling of blood cells to the matrix. Still other potential bonding agents that can be considered are phytohemaglutinin, concanavalin A, and pokeweed mitogen. It is obvious that the binding substance must be immunologically inactive with respect to any antigens or antibodies which may be present in test solutions contemplated for use.

Other substrates or matrices for use in this invention may be any convenient material which is (i) of such a character that a cell monolayer maybe irreversibly bound to it as described above; and (ii) suitable for use in view of the detection method to be used. Since the most convenient detection methods are based on light transmission—such as microscopic counting and densitometric scanning—it is preferred that a light-transmitting substrate be used. However, if counting of radioactivity is used, use of material transparent to light is obviously unnecessary.

For purposes of the present invention, the substrate or matrix may simply be the interior surface of a test tube. If a densitometric scanning procedure is to be used to evaluate the test results, a flat surface is appropriate. For purposes of large scale blood typing, strips of matrix having cell binding properties can be used to prepare the first layer of known cells. Subsequently, specific antibodies can be immunoadsorbed and tested for their capacity to bind a second layer of cells of unknown type.

Formation of Antibody Layer

The bound monolayer of red blood cells is stable and will, in turn, serve as an immunoadsorbant to bind antibodies from an applied solution (or serum) which are specific to antigenic sites on the membranes of the bound RBC. Since antigen-antibody reactions are reversible, enhancement of antibody binding is preferred. One method of enhancing antibody retention is to reduce ionic concentration. It will be understood that the phrase "reduced ionic concentration" is given its ordinary meaning in the medical art, as an ionic concentration less than that encountered in a normal saline solution. We prefer to dilute at least 1:2 in a 1.9% glycine solution, pH 7.0. This allows all weakly-binding antibodies thus far encountered to combine with the primary monolayer, and to remain bound while unwanted proteins, as well as unwanted antibodies of other specificity, are washed away with fresh glycine. Incubation at 37° C. for 20 minutes is adequate for antibody binding. Hemagglutination does not occur at this stage because the primary erythrocytes are fixed in position on the solid matrix.

Complement for $C_3$ or $C_4$ antiglobulin tests likewise can be applied, preferably in reduced ionic concentration. For either Ig or C-component antiglobulin tests, the primary monolayer, after application of Ig or C component determinants in low ionic concentrations, is washed with saline (0.9% NaCl) and then exposed to specific anti-Ig or anti-C component antiserum at normal ionic concentrations. Except for application of antibody and complement, antiglobulin tests are not improved by reduction in ionic concentration.

Formation of the Second Cell Monolayer. In the preferrd embodiment of the present invention, the test is completed by forming a second cell monolayer cross-linked to the first cell layer in an orderly one-to-one relationship by means of antibodies. As already pointed out, if the immunological type of both the cell monolayer and the antibody layer are known, the formation or non-formation of a second cell layer can be used to assay the immunological type of the cells forming the second layer. On the other hand, if the immunological specificity of both the first cell layer and the applied antibodies are unknown, the ability to form a second cell monolayer with the same cells can be relied on as a means for determining whether or not there had been formed a layer of antibodies immunoadsorbed by antigens onto the first cell layer. In either event, the second cell layer is preferably formed employing techniques to promote immunoadsorption.

For example, a very light cell suspension is applied and allowed to settle under gravity for 25 minutes. This results in a single monolayer that rests loosely over the lysed primary monolayer, but will not allow antibody cross-linking for many testing systems. It is usually inadequate unless the second layer of intact cells is brought into extremely close contact with the lysed primary monolayer.

The desired adherence can be brought about in one embodiment of this invention by the use of an asymetric colloid such as K-90 PVP. As described by Burkhart et al., supra, liquid phase antiglobulin tests are sharply augmented by K-90 PVP, and this is equally true of solid-phase antiglobulin tests. After the second layer of cells has settled, K-90 PVP (for example 2% in saline) can be gently added so as not to disturb the settled second layer of cells, and allowed to rest at ambient temperature (for example, 10 minutes). In the presence of PVP, the second layer cells become adherent to the first, even if specific antibody and/or antigen is absent. This non-specific adhesion is then eliminated by adding saline and rocking the sample back and forth just a few times. Saline plus the motion completely dislodges second layer cells in the absence of antibody and/or antigen while allowing antibody cross-linked cells to remain bound.

An alternate and superior approach is to augment adherence of second layer red cells to the primary monolayer by protamine sulfate. When protamine sulfate is used, pretreatment of the first monolayer of cells with a protease is unnecessary. This is an obvious advantage when it is necessary to assay antigens on the cells which are affected by protease.

When protamine sulfate is used to augment second layer adherence, the first monlayer is formed exactly as described above except for the omission of unneeded protease treatment. Thereafter, antibody serum is appplied to the first cell monolayer under low ionic conditions. After washing and lysing the first monolayer having immunoadsorbed antibodies, the second monolayer is applied, and adherence of the second layer is augmented with protamine sulfate. Thereafter, nonadherent cells are washed away and the test result is read.

A negative control is essential for all augmented solid-phase hemagglutination tests. The purpose of this control which is conducted in parallel with each test is to monitor the rocking motion used to dislodge the second layer cells; when the control has lost its color, the rocking is stopped. The control for indirect antiglobulin tests is the absence of anti-red cell antibody and not the absence of antiglobulin reagent. The reason for this is that the washed red cells from normal persons carry IgG, C3 and C4 molecules in small numbers, and this "weakly positive" control must be rocked until its color disappears.

No control capability exists for direct antiglobulin tests, and much less antiglobulin antibody (less than 5 $\mu$g/ml) must be used to minimize the antiglobulin agglutination properties of normal cells. Indeed, the sole available control for direct antiglobulin tests is a parallel test of cells from a "normal" person, and these vary somewhat.

Detection Methods. A variety of detection methods are suitable for use in the present invention. Erythrocytes contain their own label, namely pigmented protein (hemoglobin) which has a maximum absorbence at 415 nm. The presence or absence of erythrocytes, therefore, can be conveniently detected by means of densitometry using well-established laboratory equipment which is readily available. Alternately, if erythrocytes are used to form the second layer, the second layer can be lysed, and the released hemoglobin can be measured. Other labeling techniques can be used equally well if desired. Such techniques include the use of radioactive labels (for example $^{51}$Cr, $^{125}$I), biochemical techniques (for example, a selected intracellular enzyme), or fluorescent detection procedures (for example, using a molecular probe to identify either a living or a dead cell).

In the typing of blood cells several questions are important:
1. Are the cells in question positive or negative?
2. If the cells are positive, how strongly positive are they?
3. If the cells are positive, what percent are positive?

The first question can be answered by direct application of one of the detection methods described above to see whether a second cell layer has been formed. To answer the second question, if antibody is immunoadsorbed at an appropriate antibody concentration, the binding of the second layer of cells reflects the strength of expression of their antigens. To answer the third question, excess antibody can be applied for immunoadsorption, so that a binding of a restricted second cell monolayer is maximized. Under these conditions, submaximal bonding is a direct reflection of erythrocytes lacking specific antigens, and therefore unbound by immunoadsorbed antibody.

In forming the second cell layer, the cell suspension applied to the antibody-coated primary monolayer when carrying out such tests, have a concentration just sufficient to allow settling of a second monolayer. The second layer is then washed to remove unbound cells and, after this washing, the degree and distribution of the bound portions of the second layer becomes a function of the percentage of "positive" cells which adhere and of "negative" cells which do not adhere. The holes which result can also be detected in microscopic scanning densitometry, and their frequency and extent can be expressed as a ratio of the scanned surface.

Treatment of the Cells. The cells which may be used in the present invention may be either treated or normal, and as already indicated, may be either of known or unknown type depending upon the objectives and format of the assay. The treatment of the cells will depend upon the kind of cells which are used.

For example, in typing erythrocytes, as is known, the erythrocytes may be treated with agents which potentiate agglutination. There are a number of procedures now used in liquid-phase tests which will be equally or more successful in the solid-phase agglutination in accordance with the present invention. These include optimum use of additives that are known to potentiate agglutination, for example, symmetrical and asymmetrical hydrophilic colloids, proteases, polyelectrolytes, and buffer systems to control pH, as well as control of ionic concentration and tonicity. Such liquid-phase systems are described, for example, in Berkman et al., *Transfusion*, 11:317 (1971).

Ionic concentration may be controlled by the use of isotonic saccharides, amino acids, citrates, etc. We prefer to use a 1.9% glycine solution at pH=7.

As an example of an asymmetrical hydrophilic colloid, we have obtained good results using polyvinylpyrrolidone of an average molecular weight of 300,000, known commercially as K-90 PVP.

Similarly, we have had success in using bromelin as a protease in a concentration from about 0.005% to about 0.5% for a period of about one minute. In connection with protease treatment, it should be noted that it may destroy the antigen to be assayed. If a protease other than bromelin is used, the conditions should be modified to achieve a very light treatment.

As a polyelectrolyte, although polybrene will work, we prefer to use protamine sulfate, as an 0.2% solution to augment second layer red cell adherence.

An important advantage of the present invention is that we may use a number of agglutination potentiation reagents in an optimal and sequential manner, removing unbound and unwanted materials after each application. In the present invention, because the first cell monolayer is irreversibly bound, the cells can be washed to remove unbound prior applied reagents at each step of the process.

For example, the erythrocytes forming the primary monolayer may be treated with protease prior to application to the substrate. The protease-treated cells are centrifuged, washed, resuspended and then employed to form the primary monolayer. The primary cell monolayer, after being bound to the substrate, can then be treated with a polyelectrolyte, and the polyelectrolyte-treated layer is washed again with isotonic saline. The antibody is applied, and the remainder of that serum is also removed by washing. The cell layer at this point is hypotonically lysed by treating it with distilled water. As already noted, an alternate procedure which may be considered is to lyse the cells forming the primary monolayer at an earlier stage.

It should be noted, particularly when employing a primary monolayer of erythrocytes, that it is preferred to lyse the erythrocytes to release the hemoglobin and render the monolayer transparent. This will facilitate the ultimate reading of the test result which preferably depends upon the formation of a second erythrocyte monolayer.

The typing of platelets also requires a treatment to modify the platelets so that they will be bound onto the substrate as a monolayer. Fresh, normal platelets tend to clump when packed by centrifugation. They will, when washed, bind (as clumps) to fibrinogen that has been treated with thrombin. Treating the platelets with aspirin eliminates clumping on centrifugation but reduces their capacity to bind to thrombin. We have successfully treated platelets by first concentrating the platelets from fresh whole blood into a platelet-rich plasma. The platelet-rich plasma is treated with aspirin. The aspirin acetylates the platelets, which are then separated from the plasma, washed and resuspended in isotonic saline, and applied to a fibrinogen-polylysine-treated substrate. The acetylated platelets will form a uniform monolayer on this substrate.

When the present invention is applied to the typing of lymphocytes, we have found that lymphocytes will bind readily in the form of a monolayer to a fibrinogen-polylysine-treated substrate. No special treatment is required.

It should be noted that in the present invention, the binding of antibody by immunoadsorbence to a layer of cells provides several important advantages. Firstly, sera with concentrations of antibodies too low for conventional liquid-phase tests can be used successfully because their specific antibody content can be concentrated as bound antibody on the monolayer of cells. Secondly, under circumstances where undiluted sera cannot be used for liquid-phase tests because of other interfering serum proteins, such interference is abolished in solid-phase tests by selective adsorption of the antibody to be tested and washing to remove the interfering proteins. Thirdly, many sera are useless for liquid-phase tests because they contain non-removable antibodies with unwanted specificity. In the present invention, by appropriate selection of cells to form the first layer, it is possible to absorb only the antibodies which are to be tested.

It should be noted that the present invention also has application to other problems involving immunospecific cellular reactions. One such are antiglobulin tests to evaluate cells for their coating by IgG, IgM, IgA, IgD and IgE immunoglobulin heavy chains, $\kappa$ and $\lambda$ light chains, or by $C_3$, $C_4$ and other complement components and their fragments (see Rosenfield, et al., Vox-Sang., 26:289-333, 1974). Another application would be solid-phase tests, with quantitative evaluation, of both passive and reversed passive hemagglutination tests. Passive hemagglutination assays can be used for direct analysis of antibody concentration and also for indirect analysis of soluble antigen concentration by competitive binding on the basis of shared antigens (Nusbacher, et al., *J. Immunol.*, 108:893, 1972). Reversed passive tests measure soluble antigen directly (Cook, *Immunol.*, 8:74, 1965, and Juji and Yokochi, *Japan, J. Exptl. Med.*, 39:615, 1969). Furthermore, just as blood cells can be tested for their susceptibility to antibody-mediated agglutination or lysis by solid-phase tests, bacteria, protozoa, fungi, and cultured cell-lines from either tissues or tumors can be analyzed for antigenic constituents on their surface by the solid-phase tests described in this patent. We even anticipate using solid-phase tests ultimately to solve problems concerned with molecular antibody concentration, K value of antibody binding, and degree of K value heterogeneity.

Another valuable advantage of the present invention is the ability to type aged erythrycotes. Using previously-known procedures, it was generally believed that if erythrocytes from some persons were stored for one to three weeks, they could not be accurately typed with weak reagents. Surprisingly, we have been able to type erythrocytes which had been stored for over 6 weeks just as well as freshly-obtained erythrocytes.

The present invention, applied to tests of erythrocytes, has provided a working sensitivity equal to or exceeding the sensitivity of AutoAnalyzer tests published by Berkman et al. and by Rosenfield et al. while retaining all of the valuable benefits of quantitative data. This, coupled with the capacity to test all sources of erythrocytes, including samples aged in 4° C. storage, to immediately quantitate mixed (Ashby) agglutination, and to allow the accurate testing of single cohorts in mixtures of cells is truly unique in blood banking serology. When instrumented, these benefits of the present invention are expected to become equally valuable in tests of platelets, lymphocytes and granulocytes.

EXAMPLES

The following are examples of the practice of the present invention:

EXAMPLE 1

Immune lysis by human anti-A. Using "Falcon" polystyrene test tubes (10 mm I.D.×75 mm), we have applied 0.2 ml fibrinogen solution (0.5 mg/ml) for 2 minutes followed, after washing, by application of 0.2 ml of a poly-DL-lysine HBr solution, ~140,000 M.W. (0.1 mg/ml) for 2 minutes. After additional washing, 0.2 ml 2-5% (v/v) suspension of type $A_1$ cells in 0.9% NaCl was applied for 2-10 minutes. This resulted in the adherence of a flat-surface monolayer of red cells with a density of $2 \times 10^6/cm^2$ (2 minutes) or a flat-plus-edge surface monolayer (5-10 minutes). These red cells remained adherent despite numerous washings, and despite application of strong human anti-A. If, after application of anti-A, 0.2 ml complement was applied, hemoglobin of the adherent red cells was released, and the degree of immune lysis observed was measurable, either as retained or released hemoglobin or as retained or released radioactivity in the form of $^{51}Cr$ employed to label the cells used to construct the monolayer. With a standard dose of complement the lytic potential of anti-A could be measured quantitatively. Alternatively, with a standard dose of anti-A, lytic complement could be defined and measured by titration in toto, via the classical pathway of complement action.

None of these approaches to the study of human A-anti-A lysis can be performed sensitively and reproducibly by usual fluid-phase tests. IgM, IgG, and IgA anti-A are all very efficient agglutinins of type $A_1$ cells, and agglutination interferes with immune lysis. By solid-phase approach, the lytic potential of anti-A was not only measurable but detectable at a dilution 50 times that discernible by fluid-phase tests.

The diagnostic possibilities of this method are, therefore, clear. However, an alternative approach for the assay of A-anti-A mediated complement fixation having much more sensitivity is described below; see Example 7.

EXAMPLE 2

Blood typing (see ¶ A.1 above). The problems of typing human red cells, and of detecting human anti-red cell antibodies at the time of pre-transfusion compatibility testing, are considerable. Indeed, the only means of discerning some human red cell blood types by direct agglutination has required expensive and complicated instrumentation (Berkman, E. M., et al., Transfusion, 11:317, 1971). However, instrumented fluid-phase methods have been adapted to solid-phase testing where we have succeeded in achieving specific typing for Rh, Kell, Kidd, Duffy, $Xg^a$, Lewis, Lutheran, and MNSs, all generally with a sensitivity exceeding that obtained with the described instrumented fluid-phase tests.

In our original procedure, we adapted one of Berkman's original tests as follows: The monolayer of protease-treated red cells was constructed as described in Example 1. The monolayer was then exposed to 0.0025% protamine sulfate and, after washing, to known specific antibody (0.2 ml) in 1.9% glycine at pH 7.0. After washing with glycine, the primary monolayer was hypotonically lysed with distilled water. At this point, a second application of 0.1 ml red cells in 0.2% (v/v) strength was allowed to settle gravitationally as a light second monolayer. It was then possible to augment the specific antibody cross-linking of this second monolayer by introducing 2.5% PVP K/90. After 20 minutes at room temperature, the second monolayer was washed with 0.1 M phosphate-buffered 0.85% NaCl at pH 7.3 to remove non-antibody-bound negative cells but not antibody-bound positive cells.

In our more recent and preferred procedure, the first monolayer of red cells, without protease treatment, has been exposed to known specific antibody (0.2 ml) in 1.9% glycine as above, except that protamine sulfate treatment has been omitted. After washing with glycine, the primary monolayer is hypotonically lysed with distilled water, and the second layer of red cells (0.1 ml, 0.2% v/v) is allowed to settle as a light second monolayer. Specific antibody-cross-linking of this second monolayer is augmented by introducing 0.2 ml of diluted protamine sulfate (1:5 dilution in glycine of, for instance, Lilly protamine sulfate Injection USP, 10 mg/ml). After 25 minutes at room temperature, the second monolayer is washed with 0.1 M phosphate-buffered saline, pH 7.3, to remove the non-antibody-bound negative cells but not the antibody-bound positive cells.

Clearly, the possibilities for augmentation of solid-phase agglutination tests are numerous because the test procedure avoids the many problems associated with liquid-phase tests.

These solid-phase tests have proven to be extraordinarily sensitive for the detection of all IgG alloantibodies. We have achieved approximately the same working sensitivity for Rh as described previously for augmented AutoAnalyzer assays (Rosenfield et al., Ann. N.Y. Acad. Sci., 190:519, 1971).

Tests with anti-Rh were also conducted successfully with protease-treated red cells. Such tests performed on flat-bottom micro-titer polystyrene dishes allowed microscopic examination of specifically adherent red cells. Bound cells were present only if they were Rh-positive, and, in tests of artificial mixtures of Rh-positive and Rh-negative red cells, "holes" from non-adherent cells were observed to correspond in area to the percentage of Rh-negative cells in the artificial mixture. This result indicates that our invention can quantitatively ascertain the proportion of unbound cells in a blood sample, which is a crucially important problem both in assays of transfused cell survival by the Ashby method (Arch. Int. Med., 35:516, 1925) and in characterization of human chimeras (Race and Sanger, "Blood Groups in Man", Davis, 1968, pp. 475-490).

EXAMPLE 3

Direct Antiglobulin Tests (see ¶ B.2 above). These tests were performed like blood typing tests except that washed red cells from a patient with suspected acquired hemalytic anemia were used to construct both the first and second cell monolayers. First monolayers (bound by polylysine-fibrinogen) were exposed to single xenogeneic anti-human globulin diluted in saline and seven specificities were evaluated. These sera were independently specific for IgG, IgM, IgA, IgD, IgE, C3 and C4. The antibody-coated first monolayer was then hypotonically lysed and washed before applying cells to form the second monolayer.

In the original tests, binding of the second monolayer was augmented by adding 1% K-90 polyvinylpyrrolidone (PVP), average MW 300,000 in 0.9% NaCl More recently, we prefer to augment binding of the second layer by adding 0.2 ml of Lilly protamine sulfate diluted 1:5 in glycine. In this more recent procedure, the final washing for the second monolayer has been 0.1 M phosphate-buffered saline, pH 7.3.

The earlier procedure resembled that described by Hsu et al. (*Vox Sang.*, 26:305, 1974) who used PVP augmentation in liquid-phase agglutination. However, the more recent procedure obvious differs significantly. In both procedures, the positive results for solid-phase testing were distinctly superior to those of Hsu's liquid-phase instrumented tests. One patient with active acquired hemolytic anemia who, because of intense spontaneous liquid-phase agglutination in PVP, could not be typed for adherent proteins, was found to be clearly positive for IgG, IgM, IgA, IgE, C3 and C4.

EXAMPLE 4

Ig antiglobulin tests (see ¶ ¶ B.1.a and B.2 above). One need not use the same cells for formation of the second layer as were used in the formation of the first layer. The second layer, if desired, may be constructed of artificial cells which carry specific immunoglobulins or the heavy or light chains of them. By way of illustration, erythrocytes were treated with chromic chloride using the procedure of Gold and Fudenberg, *Journal of Immunology*, V. 99, p. 859 (1967). The chromic-chloride-treated cells are then coated with isolated M proteins, for example, IgG, IgM, IgA, IgD or IgE immunoglobulins or with Bence-Jones proteins ($\kappa$ or $\lambda$ light chains). The coated cells were then washed and used as specific second layer target cells for assay of specific antibodies to the proteins used for coating which had been immunoadsorbed on the cells forming the primary monolayer.

EXAMPLE 5

Complement antiglobulin test (see ¶ ¶ B.1.a and B.2 above). The primary cell monolayer was coated with antibodies to either complement component C3 or C4. Specific antisera are available for these complement components. The second layer of cells was prepared from normal erythrocytes of type O coated by exposure in the presence of fresh serum to sugar water, see D. E.

Jenkins and R. C. Hartman, "The Diagnostic Specificity of the Sucrose Analysis Test," Proc. XII Congress Inter. Soc. Hematol., p. 115 (N.Y.C., 1968).

EXAMPLE 6

Testing of Serum for Expected and Unexpected Antibodies (see ¶ ¶ A.2 and B.1.a above). A monolayer is prepared by bonding erythrocytes using fibrinogen and polylysine, and the erythrocyte layer is then washed. The monolayer is then incubated with the serum which is to be assayed to determine whether it contains antibodies, and excess is then washed away. Two tests are now required. In the first, the monolayer cells are hypotonically lysed, and a second layer of the same cells is formed, adherence of which denotes an agglutinating antibody (see A.2 above). In the second (see B.1.a above), anti-Ig is applied and, after washing to remove excess and unwanted proteins, the monolayer is hypotonically lysed. A second layer of Ig-coated cells is now formed, adherence of which denotes coating antibody on the primary monolayer cells (see Example 8).

EXAMPLE 7

Enhanced Assay for Complement Component Fixation (see ¶ B.1.b above). The present invention may also be used as an extraordinarily sensitive test for complement fixation, as illustrated in this example of complement fixation by A-anti-A.

A primary erythrocyte monolayer is bound to a substrate using type $A_1$ erythrocytes, and a layer anti-A antibody is immunoadsorbed under low ionic conditions using antibody diluted in glycine at pH 7 (1.9% glycine and 0.45% NaCl).

Originally, we then washed the test substrate to remove unused antibody serum and fresh human complement was applied, generally at a dilution of 1:25 in normal saline. After a short period of time, the ionic concentration was reduced by adding 5 volumes of 1.9% glycine in distilled water having a pH of 7. The serum was drained away, and the test area washed with additional glycine. Specific antibody to a complement component was applied (for example, anti-C4 appropriately diluted in saline). The test area was washed again to remove excess antibody, and a second layer of sugar-water-treated erythrocytes (see Example 5) was applied to determine the immunoadsorption of antibody to the complement component. Adherence of the second layer was augmented with PVP.

In our more recent procedure, after constructing a layer of $A_1$ erythrocytes, anti-A antibodies, and washing as described above, fresh human complement has been applied, generally in a dilution of 1:25, in glycine. The serum has been drained and the test area is washed with additional glycine. Specific antibody to complement is then applied in saline and the test area washed again to remove excess antibody. Sugar-water-treated erythrocytes are applied to form the second erythrocyte monolayer, in this case adherence being augmented with protamine sulfate, to determine immunoadsorption of antibody to complement.

The process is sensitive to complement fixation providing, in some cases, results up to 10,000 times the sensitivity of that which can be observed using direct lysis.

EXAMPLE 8

Assay of Duffy Antibody (see ¶ ¶ A.1 and B.1.a above). The present invention can also be employed in the assay of Duffy antibody. Duffy antibodies are generally IgM or IgG immunoglobulins. IgM immunoglobulin is a good agglutinin and provides unusually sensitive results when employed in solid-phase procedures in accordance with the present invention as the source of antibody applied to the primary monolayer of erythrocytes (procedure A.1). Duffy antibody of the IgG type, however, does not agglutinate well with PVP, unless used in very high concentration. This antibody is sensitively detected by solid-phase agglutination if the IgG antiglobulin reaction is used (procedure B.1.a). The result exceeds that reported by Rosenfield et al. (Vox Sang., 26:389-333, 1974). To form the second layer of erythrocytes for blood typing with Duffy antibody, it is simplest to employ the same cells coated with IgG Duffy antibody as were used to form the primary monolayer, but other cells carrying bound IgG antibody are also useful and may provide even more sensitivity.

With our more recent and preferred procedure, employing protamine sulfate to augment second layer red cell adherence, IgG anti-Duffy is an excellent agglutinin, and no longer requires use of IgG antiglobulin testing for its detection.

EXAMPLE 9

Assay of Antiplatelet Antibodies. The present invention may also be employed to assay antigens carried on platelets. For this purpose, the primary monolayer is formed from acetylated platelets.

Fresh normal platelets tend to clump spontaneously. This is eliminated by treating the platelets with aspirin. Fresh blood is fractionated to produce a platelet-rich plasma. The platelet-rich plasma thus collected is treated with an equal volume of an aspirin solution (20 cc of water, 18 mg aspirin and 75 mg imidizole) for 10 minutes at room temperature. See H. J. Weiss, L. M. Aledort and S. Kochwa, J. Clinical Investigation, 47:2169 (1968). The acetylated platelets are recovered by centrifugation, washed with saline, resuspended and applied to a fibrinogen-polylysine-treated substrate. The resulting cell layer is found to be substantially a monolayer of platelets.

The platelet monolayer was then incubated against a serum obtained from a patient known to be immunized against platelets to produce a layer of platelet antibodies immunoadsorbed on the platelet monolayer. To complete the test, an anti-IgG was applied which immunoadsorbed to the platelet antibodies, and thereafter Rh antibody-coated erythrocytes were applied. A positive result was indicated from formation of the layer of erythrocytes.

In addition to the assay of platelets described above, the monolayer of platelets bearing immunoadsorbed antibodies can be incubated against serum containing complement to determine whether the antibody is capable of fixing complement. There results a monolayer of platelets bearing antibody-mediated fixed complement. To complete the testing, an anti-complement component antibody is applied which is immunoadsorbed to the complement fixed onto the platelet monolayer, and thereafter a suspension of erythrocytes bearing the complement components reactive with anti-complement antibodies used are applied. For example, the sugar-water cells referred to in Example 5 are suitable. The formation of a layer of erythrocytes indicates the occurrence of antibody-mediated fixed complement on the primary platelet monolayer.

Alternatively, platelets coated with antibody and/or complement components in vivo can be acetylated, washed, and employed to construct a platelet monolayer on fibrinogenpolylysine-coated substrate. After immunoadsorbence of appropriate anti-immunoglobulin or anti-complement component, selected indicator erythrocytes (carrying immunoglobulin (see Example 4) or complement component (see Example 8)) can be applied to determine whether they will adhere. This, in effect, is a direct antiglobulin test of platelets specific in each assay for Ig or complement component.

EXAMPLE 10

Assay of Antilymphocyte Antibodies. The present invention is also applicable to the typing of lymphocytes. Lymphocytes require no special treatment, and may be applied directly to a fibrinogen-polylysine-treated substrate to form a lymphocyte monolayer.

While specific tests have not been made, we anticipate that the monolayers of lymphocytes can generally be used in accordance with the present invention by incubating the monolayer against a serum containing antibodies and thereafter forming a second layer of cells.

Because both platelets and lymphocytes are colorless, it may be preferred to form the second layer of cells from erythrocytes carrying appropriate immunoglobulins which will attach to the antibody layer formed on the primary cell monolayer. However, as is known, there are a variety of techniques for visualizing formation of layers of lymphocytes and, if desired, therefore, the target or second layer of cells can be formed from platelets or lymphocytes using such alternate techniques.

EXAMPLE 11

Assay of Artificial Passive Antigens (see ¶ B.1 above. Erythrocytes can be used as carriers of antigens normally not present on their surfaces. Such erythrocytes can be used in the present invention to investigate the ability of animals to respond to artificial, or unnatural antigens. Erythrocytes can also be used as convenient carriers for antigens, not normally present on their surfaces, which are to be used in bioassays for antibodies. Such artificial erythrocytes can be applied as the first monolayer, and the serum to be assayed is used to determine whether or not an antibody layer is immunoadsorbed by the primary monolayer.

By way of example, an artificial antigen of a polyaminoacid was formed by polymerizing tyrosine onto the surface of erythrocytes using the technique of Rimon and Sela, *Biochem. Biophys. Acta.*, 124:408 (1966). Such artificial erythrocytes were then bound to a substrate as a first monolayer as described above using fibrinogen and polylysine. Addition of antibody to the polyamino acid, obtained from rabbit, and complement will cause lysis. Without complement an antibody layer can be formed which will bind a second monolayer of cells coated with polytyrosine. Alternatively, the second monolayer of cells can be formed with cells coated with immunoglobulin from the species used to produce the antibody to the polyamino acid providing that specific antibody to this immunoglobulin has been immunoadsorbed by the primary monolayer of cells.

The present invention is particularly suitable for use in instrumented methods of analysis. For this purpose, one or more instruments might be designed for the preparation of the substrate, the preparation of the cells used to form the primary monolayer and the second layer, and the performance of the test. By way of illustration, one or more instruments might be designed to carry out the following:

I. Preparation of a Solid Matrix to Accept a Primary Monolayer:
   A. Apply fibrinogen to a polystyrene substrate
   B. Wash
   C. Apply a solution of polylysine to the fibrinogen-treated substrate
   D. Wash
II. Preparation of Cells for Primary Monolayer:
   A. Wash and suspend the primary cells in an isotonic saline solution
   B. Treat the primary cell suspension with protease
   C. Wash and resuspend the cells in saline
III. Preparation of Cells for Second Monolayer:
   A. Wash and suspend the cells for the second monolayer in an isotonic saline solution
   B. Treat the secondary cell suspensions with protease
   C. Wash and resuspend the cells in saline
IV. Performance of the Test:
   A. Apply prepared cells for the primary monolayer to the prepared solid matrix
   B. Wash away non-adherent cells
   C. Apply polyelectrolyte to primary cell monolayer
   D. Wash
   E. Apply antibody serum
   F. Wash
   G. Hypotonically lyse the primary monolayer with distilled water
   H. Apply prepared cells for the second monolayer
   I. Treat with polyvinylpyrrolidone
   J. Wash and read results In our more recent and preferred procedure, Steps II-B, II-C, III-B, III-C, IV-C and IV-D can be deleted while IV-I can be changed to substitute protamine sulfate for PVP. This is given below.

The foregoing can be carried out in a single instrument designed to prepare the substrate, primary cells and secondary cells (Parts I, II and III) concurrently (or in any desired order) and to supply each of the prepared components to the appropriate step of the performance of the test (Part IV). Alternatively, an instrument may be designed only for the steps of the test (i.e., Part IV outlined above). Prepared substrates (Part I) and the prepared cells (Parts II and III) may be either commercially supplied, prepared in separate instruments, or prepared in the laboratory separately from the performance of the test.

While the erythrocytes forming the first monolayer are indicated in the procedures described above as being lysed in Step IV-B, it will be appreciated that, if convenient, lysing may be carried out at an earlier stage in the process.

For purposes of machine simplification, or to carry out specialized, non-routine tests, it may be desirable in the foregoing process to prepare the primary cell monolayer outside the instrument. In such a case the machine to perform the test (i.e., Part IV above) would be designed or programmed to start with Steps IV-C, E or G, depending on how the primary cell monolayer had been previously prepared. It should be noted, however, that in carrying out the present invention once the primary cell monolayer has been prepared best results are obtained if the monolayer is not allowed to dry. If the monolayer is dried for more than a few hours, it loses its capacity to bind the second cell monolayer. If kept in a moist condition, the monolayer will retain good properties for a period of at least a week.

Experimentation with the foregoing procedure began with intensive efforts to duplicate AutoAnalyzer successes with bromelin and K-90 PVP. The results were exceptionally good for many substances, especially Rh, but met with expected failure in tests of Duffy and MN where the receptors are at least partially destroyed by an otherwise suitable protease such as bromelin. At this point, we turned to the second AutoAnalyzer channel of Berkman et al. (p. 4, supra), using low ionic protamine and devised a simple test system that possesses truly astonishing properties.

In our preferred procedure, the cells prepared for the primary monolayer and secondary monolayer (Steps II and III above) are prepared by merely washing and suspending the primary cells in an isotonic saline solution. Protease treatment of the cells is omitted. The test itself (Part IV) is then carried out as follows:

V. Modified Test Procedure
  A. Apply washed cells for the primary monolayer to the prepared solid matrix described in Part I above
  B. Wash away non-adherent cells
  C. Apply a serum of antibody under low ionic conditions; for example, diluted at least 1:2 in a 1.9% solution at a pH of 7.0, and incubate for 20 minutes at 37° C.
  D. Wash
  E. Hypotonically lyse the primary monolayer with distilled water
  F. Apply washed and suspended cells for the second monolayer and allow them to settle as a light monolayer
  G. Add gently sufficient protamine sulfate solution to augment immunoadsorption (for example, 0.2% protamine sulfate), and incubate for 5 minutes at ambient temperature
  H. Wash to remove non-adherent cells. For example, one can use a solution consisting essentially of four parts 0.9% NaCl and 1 part 0.2 M phosphate buffer at a pH of 3 and rock lightly a few times to dislodge the cells which have not been immunobound by the antibody
  I. Wash and read results This improved serology has a number of important advantages. Most importantly, the procedure seems to be the first universally suitable test for the demonstration of direct agglutination by all tested antibodies whether IgM or IgG, including those directed against Rh, Kell, Kidd, Duffy, MNSsU and Lewis determinants.

Second, univalent reagent serum is not a requirement. Providing that the specificities of all anti-erythrocytic antibodies in a serum are known, the specificity of adsorbed antibody can be selected by choice of the erythrocytes used to construct the primary monolayer. The blood type of the red cells employed for formation of the second layer (the unknown) is then established by their adherence (positive) or non-adherence (negative). This has proven to be of practical importance when performing extensive blood typing for many different antigenic determinants.

Third, with excess applied antibody, optical density of a positive second layer is largely a function of the percent of positive cells when a mixture is evaluated. A percentage of these cells can be approximated by their optical density in reference to an arbitrary expectation. An exact percent, however, requires the mixture to be reapplied sufficiently to create a complete second layer of antibodybound cells and to measure this optical density to obtain the true 100% value.

Fourth, such a completed second layer can be typed for another antigen by applying specific antibody, and after hypotonic lysis, a third layer of a known positive red cells. These will adhere only if the specific antibody was bound by the second layer. The first primary monolayer contributes nothing to this reaction except its physical support.

Fifth, data from current manual solid phase tests range less than 20% from the mean of replicates on different days. They are more reliable for many tests than the data reported by Berkman et al. When antibody is limited, optical density values are a direct reflection of antigen strength and reveal significant genetic dosage effects for Rh, Kidd, Kell, Duffy, MN, and even for Ss. In general, heterozygotes provide about 70% of the optical density seen with homozygotes and overlapping values do not occur. Interestingly, if one wishes to obtain genetic dosage on the second layer cells only, the primary monolayer cells should possess a strong expression of antigen. In other words, for A-anti-A the primary monolayer should be $A_1$ rather than $A_2$ cells, while for $Jk^a$-anti-$Jk^a$ the primary monolayer should be $Jk(a+b-)$ rather than $Jk(a+b+)$.

Solid phase direct agglutination is extremely sensitive to expected cross reactions. In reference to the optical density obtained with a homozygote, rabbit anti-M reacts weakly with type N red cells (9%), while rabbit anti-N reacts weakly with type M red cells (10%). Goat anti-$Le^a$ crossreacts with $Le(a-b+)$ cells (9%) but not significantly with $Le(a-b-)$ cells, while goat anti-$Le^{bH}$ crossreacts with $Le(a+b-)$ cells (10%) and very weakly with type O $Le(a-b-)$ cells (4%).

Interestingly, neither anti-S nor anti-s react with U-negative red cells, but both crossreact significantly with cells that are U-positive. In reference to the optical density obtained with homozygotes, anti-S agglutinates ss cells to 20%, while anti-s agglutinates SS cells to 23%. Such a result has been reported for S, but not for s.

Berkman et al. failed to discern genetic dosage for s, but noted quantitative results with anti-s that were related to the MN type of the tested cells. Solid phase hemagglutination disclosed no such problem and provided clear evidence for s genetic dosage.

Lastly, all tested cells and sources of antibody, regardless of age in storage, appear to be suitable for testing. Unlike liquid phase tests, effects on specific hemagglutination of storage of blood at 4° C. are minimal. In fact, even glutaraldehyde treated cells can be agglutinated, although not with much sensitivity.

The regression of optical density on antibody concentration in solid phase tests is linear when antibody concentration is transformed logarithmically. This differs sharply from AutoAnalyzer data, which are linear when optical density is transformed logarithmically, as one might suspect if the data were significantly proportional to the size of liquid phase red cell aggregates. In solid phase agglutination, the range of useful antibody dilutions extends over about two orders of magnitude, which is more useful for blood typing than the one order of magnitude range experienced with AutoAnalyzer tests.

When an antibody such as anti-A in limited concentration is first mixed with porcine A substance as inhibitor, the regression of optical density on inhibitor concentration is linear and does not extend beyond a factor of 10. Reproducible partial inhibition of anti-A can be achieved with a concentration of less than 1 $\mu$g A substance per ml. Interestingly, A substance applied to immunoadsorbed anti-A has little or no effect; it must be mixed with the anti-A prior to immunoadsorption for its action to be apparent. Similar results have been obtained using saliva to inhibit goat anti-Le$^a$. Hopefully, this form of agglutination inhibition testing will prove useful in identifying red cell antigens carried by selected structures isolated from red cell membranes.

If protamine augmentation is so uniquely useful for direct solid phase hemagglutination, can it not substitute for PVP in antiglobulin tests? It can, but the protamine must be used at higher dilutions in glycine than 1:5, and the final step in protamine augmented antiglobulin tests is reduced ionic. The results of preliminary protamine augmented antiglobulin tests show about three-fold more sensitivity than PVP augmented antiglobulin tests, but they do not significantly increase the working sensitivity of an IgG blood group antibody over what can be achieved by direct solid phase hemagglutination.

We claim:

1. A method for assaying cell type or compatibility on a solid matrix comprising the steps of
   (a) forming a first monolayer of cells irreversibly bound to a solid matrix, said cells having intrinsic or acquired antigens thereon;
   (b) contacting said layer (a) with a solution containing antibodies, whereby a layer of antibodies is bound by immunoadsorption, to the extent that the antibodies of said solution are reactive with the antigens of the cells of said first layer;
   (c) thereafter applying a suspension of second cells, said second cells having antigens thereon; and
   (d) subsequently measuring the extent of immunoadherence of said second cells by antibody bound to said first layer of cells.

2. A method according to claim 1 wherein said first layer of cells and said second cells are the cells of a first person and said solution is a serum obtained from a second person.

3. A method according to claim 1 wherein layer (c) is formed by applying cells from a cell population to be tested in a number essentially just sufficient to form a monolayer, and the extent of immunoadherence of said monolayer is a function of the percentage of tested cells that carry specific antigen.

4. A method according to claim 1 wherein said solution containing antibodies is a mixture of (i) a solution of an antibody reactive by immunoadsorption with an antigen carried by the cells of said layer (a) and (ii) a second solution or suspension to be assayed for antigenic determinants by inhibition of antibody in said solution (i).

5. The method according to claim 1 wherein the antigens of said first cell layer (a) are antigens carried by immunoglobulins or complement components bound on the surfaces of said cell population; the antibodies in said solution used in step (b) are anti-immunoglobulin or anti-complement to the antigenic determinants carried by the immunoglobulins or complement components to be assayed on said first cell monolayer; and the cells of said second layer carry antigenic determinants which are immunoadherent to the antibodies employed in step (b).

6. The method according to claim 5, wherein the immunoglobulins or complement components are bound to the cells of said cell layer (a) after the layer (a) has been constructed.

7. The method according to claim 5, wherein the cells bound in step (a) carry or are suspected to carry immunoglobulins or complement components to be assayed.

8. The method according to claim 6 wherein the layer (a) is a monolayer of platelets constructed by:
   (i) treating a solid matrix of polystyrene successively with a fibrinogen solution and a polylysine solution;
   (ii) treating a suspension of platelets with an acetylating agent and washing the acetylated platelets; and
   (iii) applying the washed acetylated platelets to the fibrinogen-polylysine-treated substrate under conditions effective to form a monolayer of platelets irreversibly bound to the substrate.

9. The method according to claim 8 wherein the immunoglobulins or complement components are bound to the platelets of cell layer (a) after the cell layer has been constructed.

10. The method according to claim 8, wherein the platelets treated with an acetylating agent carry or are suspected to carry an immunoglobulin or complement components to be assayed.

11. The method according to claim 1 wherein the cell monolayer (a) is formed by applying a suspension of said cells to said solid matrix to be coated, there being, on the surface of said matrix, reactive chemical groups effective to couple said cells to said matrix.

12. The method according to claim 11 wherein said reactive chemical groups are formed by successively treating a solid matrix of a polystyrene with a fibrinogen solution and a polysine solution under conditions effective to form said reactive chemical groups on the surface of said matrix.

13. A method for assaying cell type or compatibility on a solid matrix comprising the steps of
   (a) forming a first monolayer of erythrocytes irreversibly bound to a solid matrix, said erythrocytes having intrinsic or acquired antigens thereon;
   (b) contacting said layer (a) with a solution containing antibodies, whereby a layer of antibodies is bound by immunoadsorption to the extent that the antibodies of said solution are reactive with the antigens of the erythrocytes of said first layer;
   (c) thereafter applying a suspension of second erythrocytes, said second erythrocytes having antigens thereon; and
   (d) subsequently measuring the extent of immunoadherence of said second erythrocytes by antibody bound to said first layer of erythrocytes.

14. The method according to claim 13 wherein said first layer of erythrocytes is lysed prior to application of the second erythrocytes.

15. The method according to claim 14 wherein the erythrocytes of said first layer are lysed after application of said solution (b).

16. A method according to claim 13 wherein said first layer of erythrocytes and said second erythrocytes are the erythrocytes of a first person and said solution is a serum obtained from a second person.

17. A method according to claim 13 wherein layer (c) is formed by applying cells from an erythrocyte population to be tested in a number essentially just sufficient to form a monolayer, and the extent of immunoadsorption of said second monolayer is a function of the percentage of tested erythrocytes that carry specific antigen.

18. A method according to claim 13 wherein said solution containing antibodies is a mixture of (i) a solution of an antibody reactive by immunoadsorption with an antigen carried by the erythrocytes of said layer (a), and (ii) a second solution of suspension to be assayed for antigenic determinants by inhibition of antibody in said solution (i).

19. The method according to claim 13 wherein the antigens of said first erythrocyte layer are antigens carried by immunoglobulins or complement components bound on the surfaces of said erythrocyte population, the antibodies in said solution used in step (b) are anti-immunoglobulin or anti-complement to the antigenic determinants carried by the antibody or complement to be assayed on said first erythrocyte monolayer, and the erythrocytes of said second layer carry antigenic determinants which are immunoadherent to the antibodies employed in step (b).

20. The method according to claim 19 wherein the immunoglobulins or complement components are bound to the erythrocytes of said layer (a) after said layer (a) has been constructed.

21. The method according to claim 13 wherein the erythrocyte monolayer (a) is formed by applying a suspension of said erythrocytes to said solid matrix to be coated, there being, on the surface of said matrix, reactive chemical groups effective to couple said erythrocytes to said matrix.

22. The method according to claim 21 wherein said reactive chemical groups are formed by successively treating a solid matrix of a polystyrene with a fibrinogen solution and a polylysine solution under conditions effective to form said reactive chemical groups on the surface of said matrix.

23. A method for assaying cell type or compatibility on a solid matrix comprising the steps of
(a) forming a first monolayer of washed erythrocytes irreversibly bound to a solid matrix, said erythrocytes having intrinsic or acquired antigens thereon;
(b) contacting said layer (a) with a solution containing antibodies under conditions of reduced ionic concentration, whereby a layer of antibodies is bound by immunoadsorption to said first monolayer of erythrocytes to the extent that the antibodies of said solution are reactive with the antigens of the erythrocytes of said first layer;
(c) thereafter applying a suspension of second erythrocytes, said second erythrocytes having antigens thereon, and allowing said second erythrocytes to settle on said solid matrix as a second monolayer over said first layer of erythrocytes;
(d) after the said second monolayer has formed, adding protamine sulfate to said second suspension in an amount sufficient to promote adherence of said second erythrocytes to antibodies bound to said first monolayer; and
(e) thereafter washing to remove second erythrocytes which are not immunobound, and measuring the extent of immunoadherence of said second erythrocytes to antibodies bound to said first layer of erythrocytes.

24. The method according to claim 23, wherein between steps (a) and (b) and between steps (b) and (c), the first monolayer is washed to remove nonadherent cells and unwanted reagents.

25. The method according to claim 23, wherein following step (b) said first monolayer of erythrocytes is hypotonically lysed with distilled water.

26. A method according to claim 23, wherein said solution containing antibodies used in step (b) is a serum of antibody diluted at least 1:2 with a 1:9% glycine solution at a pH of 7.0.

27. The method according to claim 23, wherein said substrate in step (e) is washed with a solution consisting essentially of isotonic NaCl and phosphate buffer at a pH of 3.

28. A method for assaying cell type or compatibility on a solid matrix comprising the steps of
(a) forming a first monolayer of cells irreversibly bound to a solid matrix, said cells having or carrying antigens thereon;
(b) contacting said layer (a) with a solution containing antibodies capable of forming a layer of antibodies bound by immunoadsorption to said first layer of cells to the extent that the antibodies of said solution are reactive with the antigens of the cells of said layer; and
(c) thereafter measuring the extent of immunoadsorption of said antibodies by applying a second solution containing lytic complement effective to lyse the cells of said layer (a) in the presence of immunoadsorbed antibody and observing the extent of immune lysis which occurs.

29. A method according to claim 28, wherein the cells of said first layer are cells of a first person and said solution containing antibodies is a serum obtained from a second person.

30. The method according to claim 28, wherein said cell layer (a) is formed by applying a suspension of cells to said solid matrix to be coated, there being, on the surface of said matrix, reactive chemical groups effective to couple said cells to said matrix.

31. The method according to claim 30, wherein the cells of said first layer are erythrocytes.

32. The method according to claim 30, wherein said reactive chemical groups are formed by successively treating a solid matrix of a polystyrene with a fibrinogen solution and a polylysine solution under conditions effective to form said reactive chemical groups on the surface of said matrix.

33. The method according to claim 29, wherein the cell monolayer (a) is formed by applying a suspension of said cells to said solid matrix to be coated, there being, on the surface of said matrix, reactive chemical groups effective to couple said cells to said matrix.

* * * * *